(12) United States Patent
Abe et al.

(10) Patent No.: US 11,004,201 B2
(45) Date of Patent: May 11, 2021

(54) DIAGNOSIS SUPPORT PROGRAM

(71) Applicant: PARAMEVIA PTE. LTD., Singapore (SG)

(72) Inventors: Takehiko Abe, Singapore (SG); Norifumi Yoshida, Singapore (SG)

(73) Assignee: PARAMEVIA PTE. LTD., Singapore (SG)

(*) Notice: Subject to any disclaimer, the term of this patent is extended or adjusted under 35 U.S.C. 154(b) by 39 days.

(21) Appl. No.: 16/318,839

(22) PCT Filed: Feb. 28, 2017

(86) PCT No.: PCT/JP2017/007859
§ 371 (c)(1),
(2) Date: Jan. 18, 2019

(87) PCT Pub. No.: WO2018/016113
PCT Pub. Date: Jan. 25, 2018

(65) Prior Publication Data
US 2019/0287248 A1    Sep. 19, 2019

(30) Foreign Application Priority Data
Jul. 19, 2016  (JP) .............................. JP2016-141658

(51) Int. Cl.
*G06T 7/00* (2017.01)
*G06T 7/11* (2017.01)
(Continued)

(52) U.S. Cl.
CPC .............. *G06T 7/0016* (2013.01); *A61B 6/00* (2013.01); *A61B 6/5217* (2013.01);
(Continued)

(58) Field of Classification Search
CPC ......... G06T 7/0016; G06T 7/11; G06T 7/168; G06T 7/174; G06T 2207/10016;
(Continued)

(56) References Cited

U.S. PATENT DOCUMENTS 9,064,302 B2    6/2015    Muraoka et al.
9,972,088 B2    5/2018    Fujiwara et al.
(Continued)

FOREIGN PATENT DOCUMENTS

JP    2010-187723 A       9/2010
JP    2010187723 A    *  9/2010
(Continued)

OTHER PUBLICATIONS

An FPGA-Based Rapid Wheezing Detection System (Year: 2014).*
(Continued)

*Primary Examiner* — Nizar N Sivji
(74) *Attorney, Agent, or Firm* — Aslan Law, P.C.

(57) ABSTRACT

A movement of an area whose shape changes for each respiration or for each heartbeat is displayed. A diagnosis support program that analyzes images of a human body and displays analysis results, the program causing a computer to execute: processing of acquiring a plurality of frame images from a database that stores the images (S1); processing of specifying a respiratory cycle based on pixels in a specific area in each of the frame images (S2); processing of detecting a lung field based on the specified respiratory cycle (S3); processing of dividing the detected lung field into a plurality of block areas (S4) and calculating a change in image in a block area in each of the frame images (S5); processing of performing a Fourier analysis of a change in image in each block area in each of the frame images (S6); and processing of displaying each image after the Fourier analysis on a display as a pseudo color image (S7).

12 Claims, 9 Drawing Sheets

(51) Int. Cl.
*G06T 7/168* (2017.01)
*G06T 7/174* (2017.01)
*G16H 30/40* (2018.01)
*A61B 6/00* (2006.01)

(52) U.S. Cl.
CPC .............. *A61B 6/5264* (2013.01); *G06T 7/11*
(2017.01); *G06T 7/168* (2017.01); *G06T 7/174*
(2017.01); *G16H 30/40* (2018.01); *G06T*
*2207/10016* (2013.01); *G06T 2207/30061*
(2013.01); *G06T 2207/30104* (2013.01)

(58) Field of Classification Search
CPC .......... G06T 2207/30061; G06T 2207/30104;
G16H 30/40; G16H 50/20; G16H 10/60;
G16H 50/30; A61B 6/00; A61B 6/5217;
A61B 6/5264; A61B 6/486; A61B
6/5288; A61B 6/50; A61B 5/024; A61B
5/0402; A61B 5/08; A61B 6/502; A61B
6/5205
See application file for complete search history.

(56) References Cited

U.S. PATENT DOCUMENTS

| 2013/0281830 | A1* | 10/2013 | Patz | ........................ | A61B 5/004 |
| | | | | | 600/419 |
| 2016/0098836 | A1* | 4/2016 | Yamato | .............. | G06K 9/00536 |
| | | | | | 382/128 |
| 2016/0189394 | A1 | 6/2016 | Zhang et al. | | |
| 2017/0025158 | A1* | 1/2017 | Miyake | .............. | G06K 9/00496 |
| 2017/0287114 | A1* | 10/2017 | Futamura | ............... | A61B 6/541 |
| 2019/0307334 | A1* | 10/2019 | Wang | ..................... | A61B 5/721 |
| 2020/0077892 | A1* | 3/2020 | Tran | ..................... | A61B 5/6824 |

FOREIGN PATENT DOCUMENTS

| JP | 2012-192255 A | | 10/2012 |
| JP | 2012192255 A | * | 10/2012 |
| JP | 5874636 B2 | | 3/2016 |
| WO | WO 2014/192505 A1 | | 12/2014 |

OTHER PUBLICATIONS

International Search Report from corresponding PCT application No. PCT/JP2017/007859 dated Aug. 8, 2017 (1 pg).

Fujita, Hiroshi, et al., "Basic Imaging Properties of a Large Image Intensifier—TV Digital Chest Radiographic System", Investigative Radiology, vol. 22, No. 4, Apr. 1987, pp. 328-335.

Rie Tanaka "Dynamic chest radiography: flat-panel detector (FPD) based functional X-ray imaging" Japanese Society of Radiological Technology and Japan Society of Medical Physics. Published online: June 13, 2016. Japan. pp. 139-153.

Abe et al. "Evaluation of pulmonary blood flow using new method of Dynamic X-ray Examination; comparison with 99mTc-MAA perfusion scintigraphy" Japan Anti-Tuberculosis Association Fukujyuji Hospital. Japan. 18 pages.

India Office Action issued in India patent application No. 201947005462, Examination Report, India Intellectual Property Office, dated Jan. 25, 2021, 6 pages.

* cited by examiner

CHANGE IN intensity
OF FREQUENCY OMPONENTS
CLOSE TO HEARTBEAT

INVERSE Fourier
TRANSFORM

Fourier ANALYSIS RESULTS
INDICATING ONLY FREQUENCY COMPONENTS
CLOSE TO HEARTBEAT

DIAGNOSIS SUPPORT PROGRAM

CROSS-REFERENCE TO RELATED APPLICATIONS

This application is a 35 U.S.C. § 371 national phase application of PCT International Application No. PCT/JP2017/007859, filed Feb. 28, 2017, which claims the benefit of priority under 35 U.S.C. § 119 to Japanese Patent Application No. P2016-141658, filed Jul. 19, 2016, the contents of which are incorporated herein by reference in their entirety.

TECHNICAL FIELD

The present invention relates to a technique to analyze an image of a human body and display analysis results.

BACKGROUND

When a doctor diagnoses a lung by dynamic state images of the chest, important is observation of time-series chest dynamic state images in which a subject is photographed in a natural breathing state. A spirometer with which it is easy to acquire physiological data, an RI (Radio Isotope) inspection, a simple X-ray photography with which it is possible to obtain morphological data, CT (Computed Tomography), and so on, are known as a method of evaluating lung functions. However, it is not easy to acquire both physiological data and morphological data efficiently.

In recent years, a method is attempted in which dynamic state images of the chest of a human body are photographed by making use of a semiconductor image sensor, such as an FPD (Flat Panel Detector) and used for a diagnosis. For example, "Basic Imaging Properties of a Large Image Intensifier-TV Digital Chest Radiographic System" Investigative Radiology: April 1987; 22: 328-335 has disclosed a technique to generate a difference image indicating a difference in signal value between a plurality of frame images making up a dynamic state image and to find and display a maximum value of each signal value from the difference image.

Further, Japanese Patent No. 5874636 has disclosed a technique to extract a lung field area from each frame image of a plurality of frame images indicating the dynamic state of the chest of a human body and divide the lung field area into a plurality of small areas, and to perform an analysis by associating the divided small areas to each other between the plurality of frame images. With this technique, a feature amount indicating the movement of the divided small area is displayed.

NPL 1:

However, only by displaying the maximum value of the difference value between frames for each pixel of the dynamic state image as in the technique described in Japanese Patent No. 5874636, it is not easy for a doctor to grasp the state of a disease. Further, only by displaying the feature amount as in the technique described in the above mentioned reference, it is also not sufficient to grasp the state of a disease. Consequently, it is desirable to display images in accordance with the state of respiration and lung blood vessels. That is, it is desirable to grasp the breathing state and the entire dynamic state of blood vessels of a human body, which is a subject, and based on respiration, blood vessels of the heart and the hilum pulmonis portion, or the waveform or frequency of blood flows, to display images indicating the movement corroborated by those.

SUMMARY OF THE INVENTION

The present invention has been made in view of the aforementioned circumstances and has an object to provide a diagnosis support program capable of displaying the movement of an area whose shape changes for each respiration or for each heartbeat. More specifically, it has an object to generate images that assist a diagnosis by calculating numerical values that assist a diagnosis by digitizing the concordance rate or another non-concordance rate for the waveform and Hz already acquired for new target data to be measured and further by turning these numerical values into images.

In order to achieve the above-described object, the present application has taken steps as follows. That is, a diagnosis support program according to an aspect of the present invention is a diagnosis support program that analyzes images of a human body and displays analysis results, and causes a computer to execute processing of acquiring a plurality of frame images from a database that stores the images; processing of specifying a respiratory cycle based on pixels in a specific area in each of the frame images; processing of detecting a lung field based on the specified respiratory cycle; processing of dividing the detected lung field into a plurality of block areas and calculating a change in image in a block area in each of the frame images; processing of performing a Fourier analysis of a change in image in each block area in each of the frame images; and processing of displaying each image after the Fourier analysis on a display.

Further, a diagnosis support program according to an aspect of the present invention is a diagnosis support program that analyzes images of a human body and displays analysis results, and causes a computer to execute processing of acquiring a plurality of frame images from a database that stores the images; processing of specifying a blood vessel beat cycle of a subject; processing of specifying a respiratory cycle based on pixels in a specific area in each of the frame images; processing of detecting a lung field based on the specified respiratory cycle; processing of dividing the detected lung field into a plurality of block areas and calculating a change in image in a block area in each of the frame images; processing of performing a Fourier analysis of a change in image in each block area in each of the frame images based on the specified blood vessel beat cycle; and processing of displaying each image after the Fourier analysis on a display.

Further, a diagnosis support program according to an aspect of the present invention is a diagnosis support program that analyzes images of a human body and displays analysis results, and causes a computer to execute processing of acquiring a plurality of frame images from a database that stores the images; processing of specifying a blood vessel beat cycle of a subject; processing of dividing an analysis range that is set for each of the frame images into a plurality of block areas and calculating a change in image in a block area in each of the frame images; processing of performing a Fourier analysis of a change in image in each block area in each of the frame images based on the specified blood vessel beat cycle; and processing of displaying each image after the Fourier analysis on a display.

Further, a diagnosis support program according to an aspect of the present invention specifies a respiratory cycle of a subject based on a movement of a diaphragm, a movement of a thorax, or other pieces of data including a spirogram.

Further, a diagnosis support program according to an aspect of the present invention specifies a blood vessel beat cycle of the subject based on measurement results by other modality devices including an electrocardiogram or a pulsimeter, and alternatively, extracts a movement of a diaphragm and a thorax and specifies a respiratory cycle of a subject based on an image of a diaphragm and an image of a thorax at least included in each of the frame images, detects a lung field based on the specified respiratory cycle, specifies a position of a heart, a position of a hilum pulmonis, and blood vessel cycles of a main lung blood vessel and a large blood vessel from the detected lung field, and specifies a blood vessel beat cycle based on a change in image of each specified region.

Further, a diagnosis support program according to an aspect of the present invention calculates a relative position relationship between an inside of a lung field and blood vessels based on the specified respiratory cycle and specifies a shape of a lung of a subject as a standard lung and specifies a dynamic state of a blood flow of the subject as a standard blood vessel area.

Further, a diagnosis support program according to an aspect of the present invention divides a lung field into a plurality of block areas by plotting a plurality of points in accordance with a fixed rule on opposing contours of a lung field and by connecting opposing points by a segment.

Further, in a diagnosis support program according to an aspect of the present invention, the processing of performing a Fourier analysis Fourier-transforms an image in each block area in each of the frame images and performs inverse Fourier transform by extracting only waveforms substantially indicating a respiratory cycle or a blood vessel beat cycle from a waveform after Fourier transform.

According to an aspect of the present invention, it is made possible to display a movement of an area whose shape changes for each respiration or for each heartbeat. That is, by calculating numerical values that assist a diagnosis and further by turning these numerical values into images, it is made possible to generate images that assist a diagnosis. As a result of this, it is made possible to visualize a difference between a normal movement and an abnormal movement and to visually recognize the difference, and therefore, this is appropriate for the field of the image medical practice.

DESCRIPTION OF EMBODIMENTS

Figure 1A:
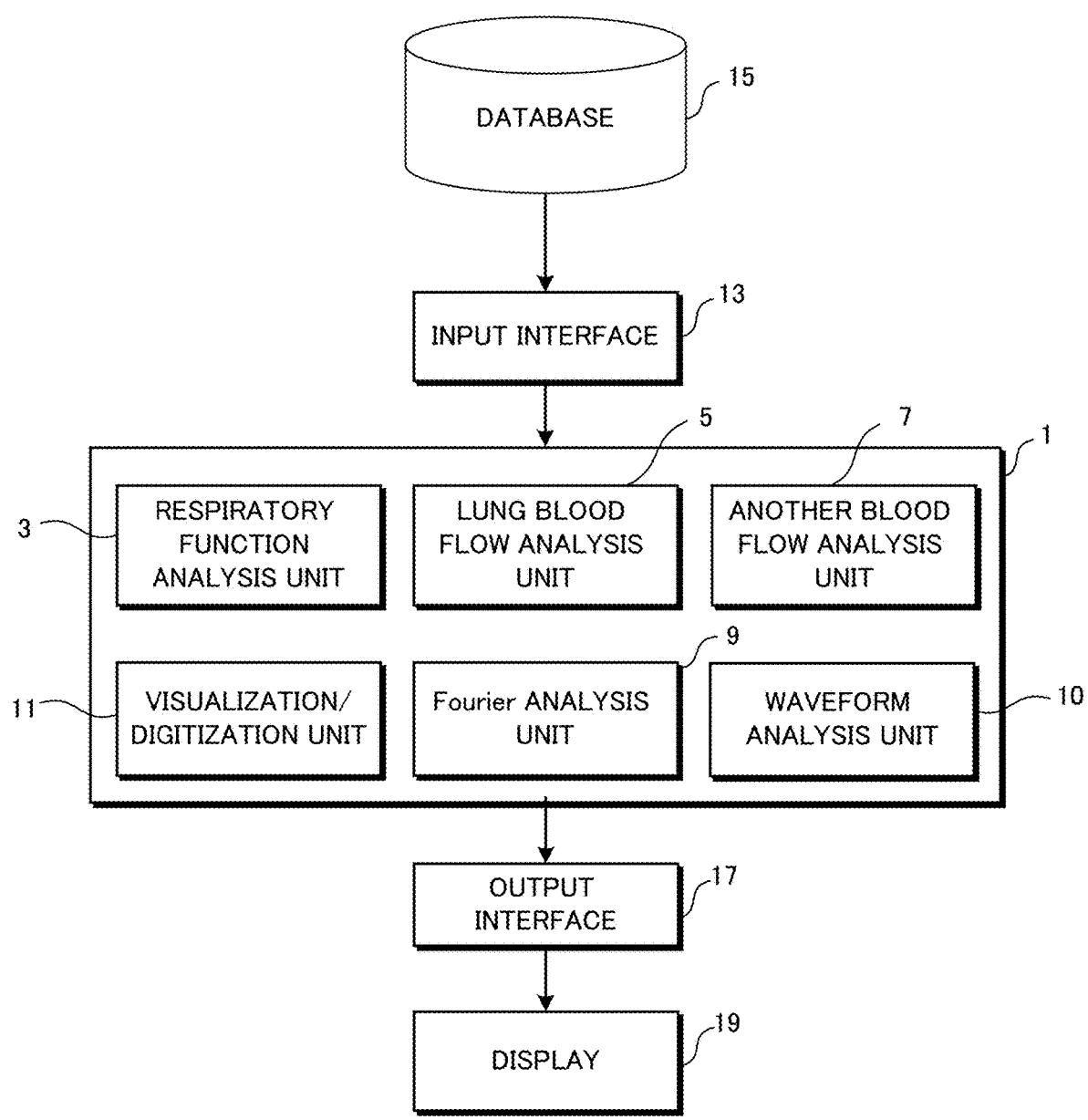
FIG. 1A is a diagram illustrating an outline configuration of a diagnosis support system according to the present embodiment.

First, the basic concept of the present invention will be explained. In the present invention, for movements that can be captured so as to repeat in a fixed cycle in respiration and biological movements of blood vessels and others in a human body, a fixed iteration or a fixed movement (routine) on the time axis in the entire or partial range is captured as a wave and measured.

For measurement results of a wave, (A) a form of the wave itself or (B) intervals (Hz) of the wave are used.

Waves that are linked similarly during the same period of time may exist. For example, in the case of respiration, an approximation as follows may be considered.

(average of change in density in a rough area)≈(change in thorax)≈(movement of diaphragm)≈(lung function inspection≈(thoracoabdominal respiration sensor)

By using any of these pieces of data or data obtained by combining these pieces of data, it is made possible to extract an image with higher accuracy. At this time, there is a case where calculation is mutually performed a plurality of times. In this case, the artifact for the results is removed again and extraction of the function is performed by extracting from the extracted waveform of new data, the data waveform that becomes the first base, the waveform of another modality and the like, the waveform of the ambience, and the waveform of a plurality of times. At this time, the number of times may be one or more.

Here, when base data is created, by a plurality of modalities (for example, two or more of a fixed density, volumetry, movement of a thorax, movement of a diaphragm, spirometry, and thoracoabdominal respiration sensor) or a plurality of times of waveform measurement of the same respiratory cycle, the mutual component extraction is complemented for each other, and thereby, accuracy is improved. Due to this, it is made possible to reduce the artifact and to improve the accuracy based on a fixed prediction of a line and the like.

Further, fluctuations in axis, width, range, and Hz due to the mutual component extraction and the width are estimated. That is, by a plurality of times of superimposition, the axis setting of Hz is averaged and the optimum range of the axis, width, range, and Hz is calculated by the variance. At this time, there is a case where Hz (noise) of another behavior is extracted and if its wave exists, the degree in which the wave is not included is measured relatively.

By the above, it is made possible to obtain master data. For the above-described master data, a new target desired to be measured is extracted in a fixed width and range of the waveform of the above-described master data and Hz of the wave. For example, only respiration is extracted or extraction is performed in the width and range as the framework of the degree of blood vessel extraction. Note that this waveform and the width of Hz are determined relatively and comprehensively based on statistics by using the waveform element in another function, the artifact, such as noise, the waveform of another modality deemed to have another conformity, the reproducibility performed a plurality of times, and so on. Then, adjustment and experience are required (it is also possible to apply machine learning). The reason is that while the width and range are extended, the element of another function begins to enter, if the width and range are too narrow, the element of the function itself is eliminated, and therefore, as to the range, adjustment is necessary. For example, in the case where there is data of a plurality of times, it is easy to specify the range, concordance width between Hz and measurement, and so on.

Next, for the data of the new target desired to be measured, by digitizing the waveform originally captured and the concordance rate or another non-concordance rate for Hz, the numerical values that assist a diagnosis are calculated. For example, it is made possible to apply to a diagnosis auxiliary device by measuring the waveform matching rate of the master disease and calculating the concordance rate of the disease waveform as well as removing noise in the pulsimeter and stethoscope.

Further, for the data of the new target desired to be measured, by turning the waveform originally captured and the concordance rate or another non-concordance rate for Hz into images, the images that assist a diagnosis are calculated. For example, the difference between the normal deglutition and that of a patient is visualized and the difference between the behavior conventionally performed and that currently performed is displayed. For example, a change, a difference, and so on, in how to move one's feet in walking and swing.

The extracted amount of change is visualized and extracted as an image. This is the respiratory function analysis and the blood vessel analysis to be explained below. Then, the change rate of the thorax and the diaphragm is visualized. At this time, there is a case where the artifact for the results is excluded again and extraction of the function is performed by extracting from the extracted waveform of new data, the data waveform that becomes the first base, the waveform of another modality and the like, the waveform of the ambience, and the waveform of a plurality of times.

Further, there is a case where the feature amount is grasped by those from which the change components extracted from other than the above are excluded. For example, when the movement of the abdominal intestinal tract is grasped, an attempt is made to extract the movement of the abdominal intestinal tract by excluding the influence of respiration and the influence of blood vessels from the abdomen.

Further, by correcting the image (CT, MRI, special roentgenography, PET/scintigraphy, and so on) that requires a fixed photographing time by the change rate due to the extraction, a clearer and more accurate image is provided. This is effective in, for example, correction of the ascending aorta heart, correction of the heart figure, correction in fluctuations in the bronchial tube, evaluation of the surroundings of the thorax, and photographing in the state where breath cannot be held (several minutes are required for a patient and photographing).

Hereinafter, an embodiment of the present invention will be explained with reference to the drawings. FIG. 1A is a diagram illustrating an outline configuration of a diagnosis support system according to the present embodiment. This diagnosis support system exhibits a specific function by causing a computer to execute a diagnosis support program. A basic module 1 includes a respiratory function analysis unit 3, a lung blood flow analysis unit 5, an another blood flow analysis unit 7, a Fourier analysis unit 9, a waveform analysis unit 10, and a visualization/digitization unit 11. The basic module 1 acquires image data from a database 15 via an input interface 13. In the database 15, for example, images by DICOM (Digital Imaging and COmmunication in Medicine) are stored. An image signal output from the basic module 1 is displayed on a display 19 via an output interface 17. Next, the function of the basic module according to the present embodiment will be explained.

In the present embodiment, based on the following indexes, the respiratory cycle is analyzed. That is, the respiratory cycle is analyzed by using at least one of density/intensity in a fixed area within the lung field, the movement of the diaphragm, and the movement of the thorax. Further, it may also be possible to use the data obtained from the range consisting of fixed volume density/intensity measured in a region where permeability of X-ray (further, a plurality of kinds of modality, such as CT and MRI) is high and obtained by other measurement methods, such as spirogram. Note that it is desirable to improve accuracy of data by comparing the analysis results for each respiration and analyzing the tendency from a plurality of pieces of data.

In the present embodiment, based on the following indexes, the blood vessel beat is analyzed. That is, the heart/position of hilum pulmonis/main blood vessel are specified from the measurement results of other modalities, such as an electrocardiogram and a pulsimeter, or the lung contour, and the blood vessel beat is analyzed by using a change in density/intensity of each region. Further, it may also be possible to analyze a change in density/intensity of a target region by manually performing plotting on an image. Note that it is desirable to improve accuracy of data by comparing the analysis results for each beat and analyzing the tendency from a plurality of pieces of data.

From the database (DICOM), images are extracted and the lung contour is automatically detected by using the above-described respiratory cycle analysis results. For this automatic detection of the lung contour, it is possible to use the technique known conventionally. For example, it is possible to use the technique disclosed in Japanese Patent Laid-Open No. S63-240832 or Japanese Patent Laid-Open No. H2-250180.

Next, the lung field is divided into a plurality of block areas and a change in each block area is calculated. Here, it may also be possible to determine the size of the block area in accordance with the photographing speed. In the case where the photographing speed is slow, it becomes difficult to specify a corresponding region in a frame image next a certain frame image, and therefore, the block area is made large. On the other hand, in the case where the photographing speed is fast, the number of frame images per unit time is large, and therefore, it is made possible to follow even when the block area is small. Further, it may also be possible to calculate the size of the block area in accordance with which timing of the respiratory cycle is selected. Here, there is a case where it is necessary to correct a deviation in the lung field area. At this time, the movement of the thorax, the movement of the diaphragm, and the position relationship of blood vessels of the entire lung field are identified, and further, the relative position of the lung contour is grasped, and evaluation is made relatively based on the movement. Note that, when the block area is too small, there is a case where a flicker occurs in the image. In order to prevent this, it is necessary for the block area to have a fixed size.

Figure 1B:
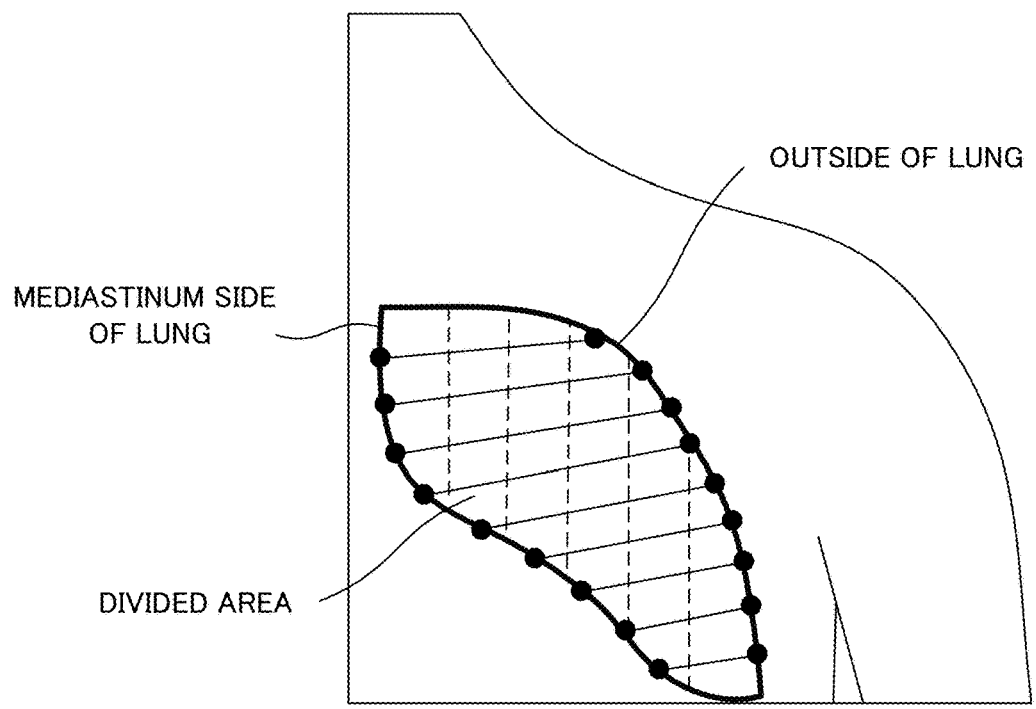
FIG. 1B is a diagram illustrating an example of a division method of a lung area.

A method of dividing the lung field into a plurality of block areas will be explained. As illustrated in FIG. 1B, a first method is a method of dividing the lung transversely by plotting points in the vertical direction of the lung. By the first method, for example, it is possible to find the distance on the mediastinum side of the lung and the distance on the outside of the lung and to plot points obtained by equally dividing the distances, respectively. Then, division is performed by determining the enlargement ratio of the mediastinum side and the outside. Note that, in the lung, the diaphragm side moves more than the pulmonary apex side, and therefore, it may also be possible to plot points whose size becomes smaller toward the diaphragm side. Further, in FIG. 1B, it may also be possible to divide the lung into a plurality of rectangular (square) block areas by additionally drawing lines (dot lines) in the vertical direction. Due to this, it is made possible to represent the movement of the lung more accurately.

Figure 1C:
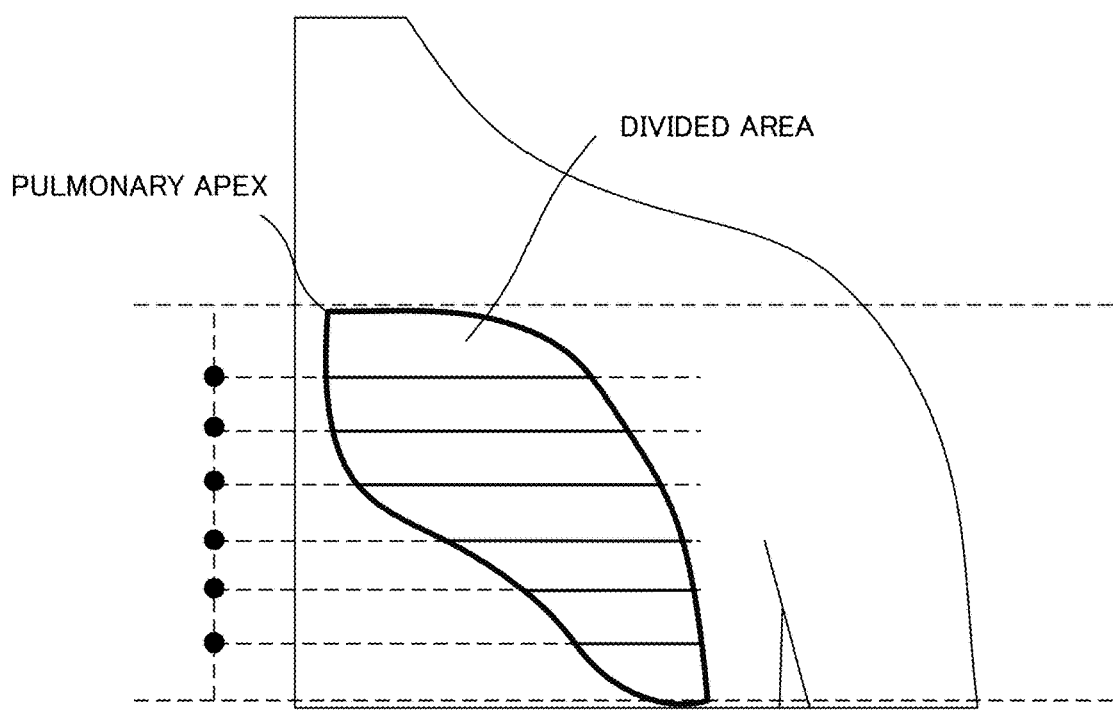
FIG. 1C is a diagram illustrating an example of a division method of a lung area.

A second method is also a method of dividing the lung transversely, but as illustrated in FIG. 1C, parallel lines are drawn between the pulmonary apex and the end portion of the diaphragm (or the vicinity thereof) in the area of the lung and a plurality of points is plotted therebetween. Then, at the portions facing each other, the enlargement ratio is determined and division is performed. In the second method, the length of the curved portion of the lung is not calculated, and therefore, there is a merit that the amount of calculation is small. Further, as illustrated in FIG. 1B, it may also be possible to divide the lung into a plurality of rectangular (square) block areas by additionally drawing lines (dot lines) in the vertical direction.

Figure 1D:
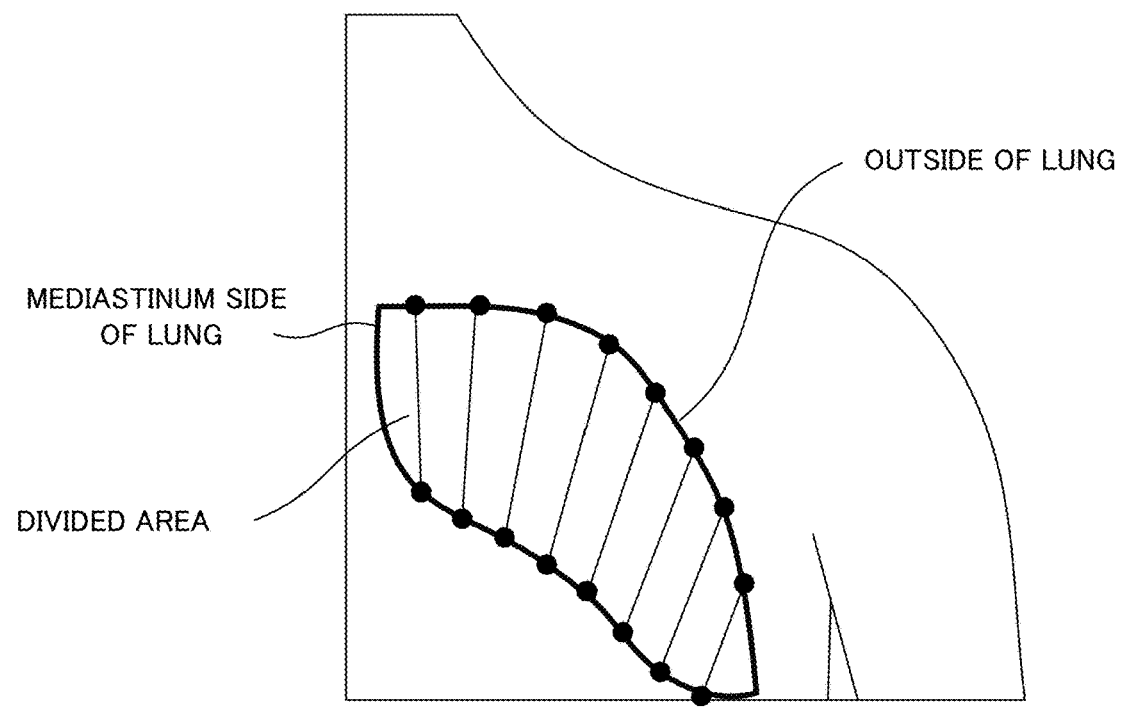
FIG. 1D is a diagram illustrating an example of a division method of a lung area.

A third method is a method of dividing the lung vertically by plotting points in the transverse direction of the lung as illustrated in FIG. 1D. With the third method, for example, it is possible to find the distance on the mediastinum side of the lung and the distance on the outside of the lung and to plot points obtained by equally dividing the distances, respectively. Then, at the portions facing each other, the enlargement ratio is determined and division is performed. Note that, in the lung, the diaphragm side moves more than the pulmonary apex side, and therefore, it may also be possible to plot points whose size becomes smaller toward the diaphragm side. Further, as illustrated in FIG. 1B, it may also be possible to additionally draw lines in the transverse direction so as to divide the lung into a plurality of rectangular (square) block areas.

Figure 1E:
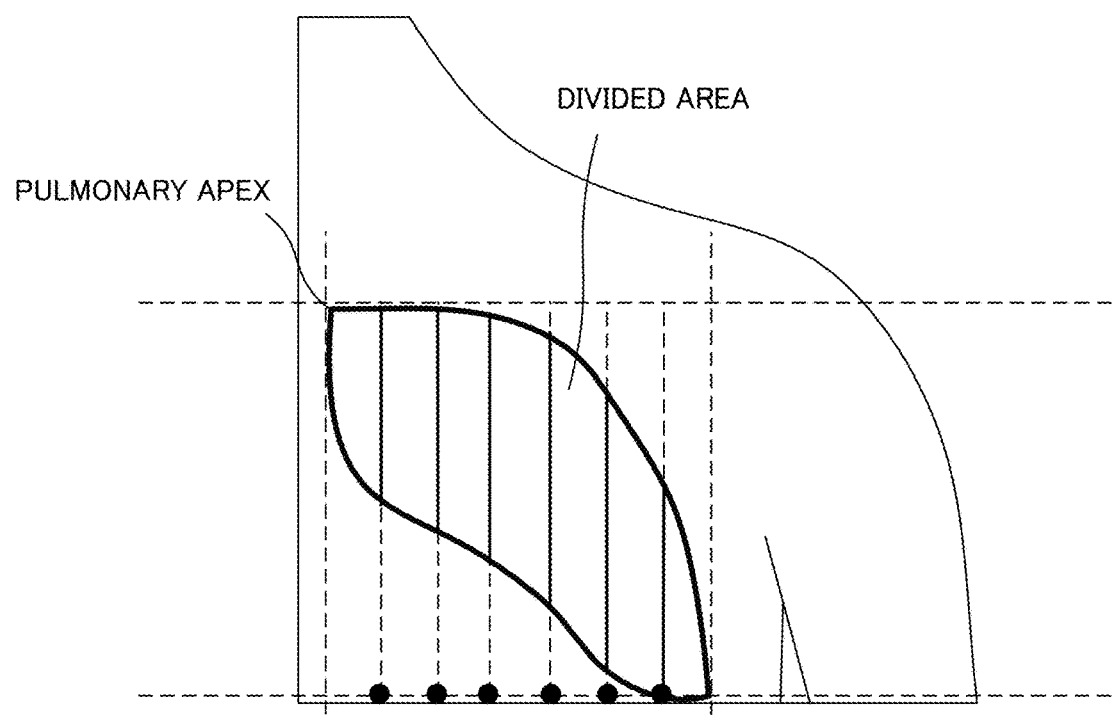
FIG. 1E is a diagram illustrating an example of a division method of a lung area.

A fourth method is also a method of dividing the lung vertically, but as illustrated in FIG. 1E, parallel lines are drawn in the vertical direction of the pulmonary apex and in the vertical direction of the end portion of the diaphragm (or the vicinity thereof) in the area of the lung and a plurality of points is plotted therebetween. Then, at the portions facing each other, the enlargement ratio is determined and division is performed. In the fourth method, the length of the curved portion of the lung is not calculated, and therefore, there is a merit that the amount of calculation is small. Further, as illustrated in FIG. 1B, it may also be possible to additionally draw lines in the transverse direction to as to divide the lung into a plurality of rectangular (square) block areas.

Figure 1F:
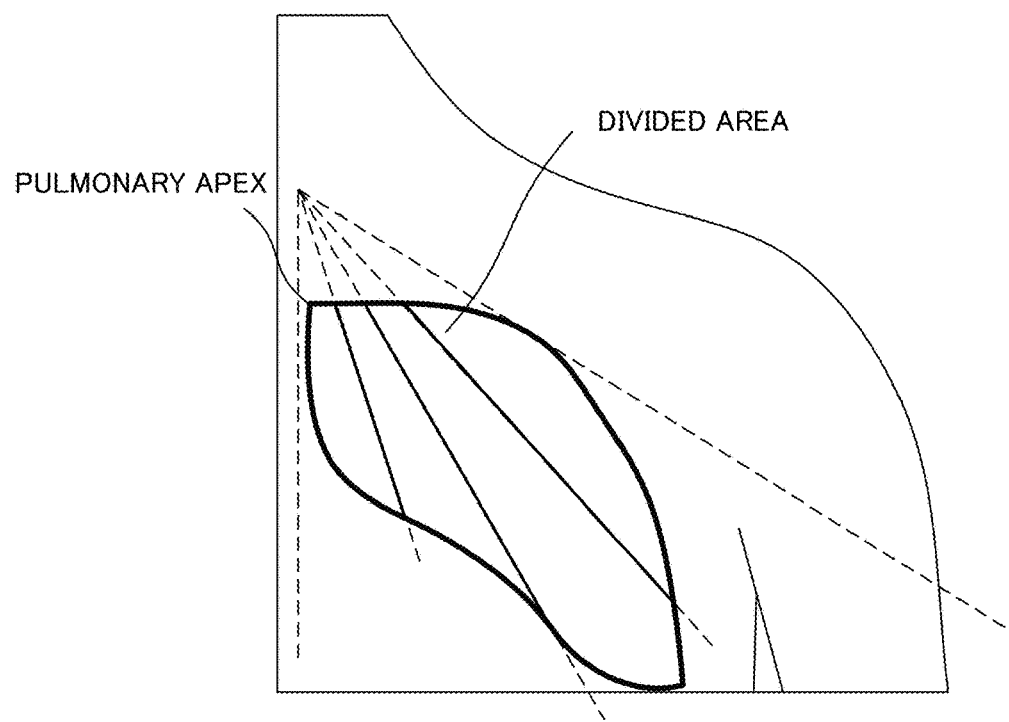
FIG. 1F is a diagram illustrating an example of a division method of a lung area.

In a fifth method, as illustrated in FIG. 1F, a tangent line at the pulmonary apex portion and a tangent line at the diaphragm are drawn and the intersection of the tangent lines is determined to be a center point and the lung is divided by segments drawn from a straight line (for example, a plumb line) including the point at fixed angle intervals. With the fifth method, depending on how to determine the center point, the division method becomes close to the transverse division of the lung or becomes close to the vertical division of the lung. Further, as illustrated in FIG. 1B, it may also be possible to additionally draw lines in the vertical direction or in the transverse direction so as to divide the lung into a plurality of rectangular (square) block areas.

Figure 1G:
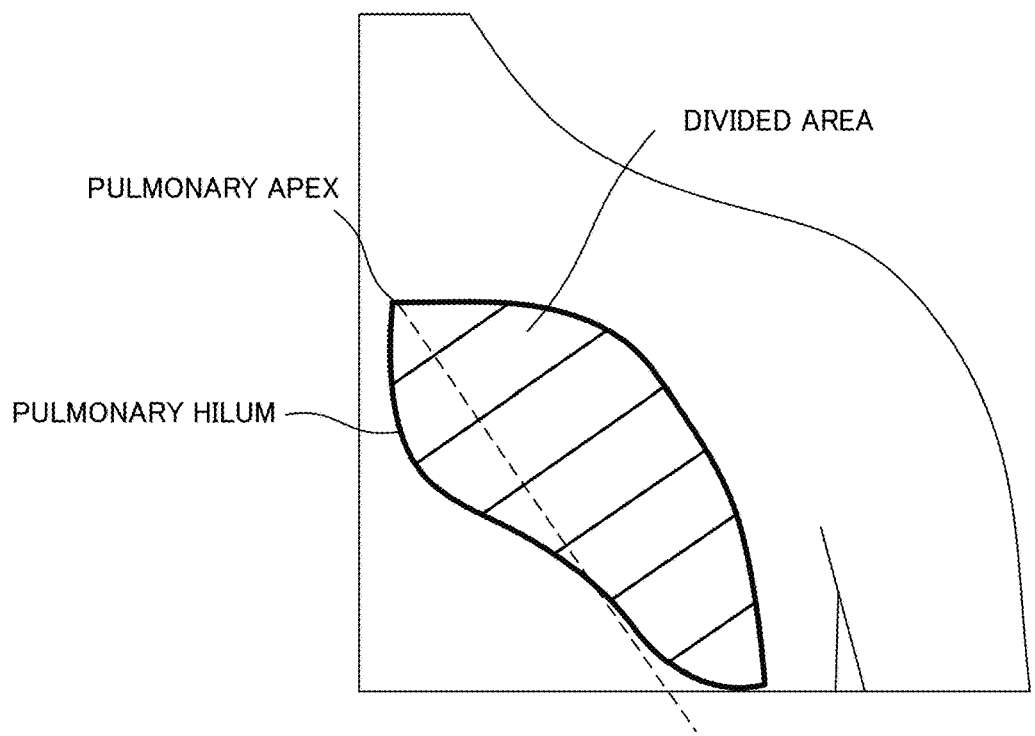
FIG. 1G is a diagram illustrating an example of a division method of a lung area.
Figure 1H:
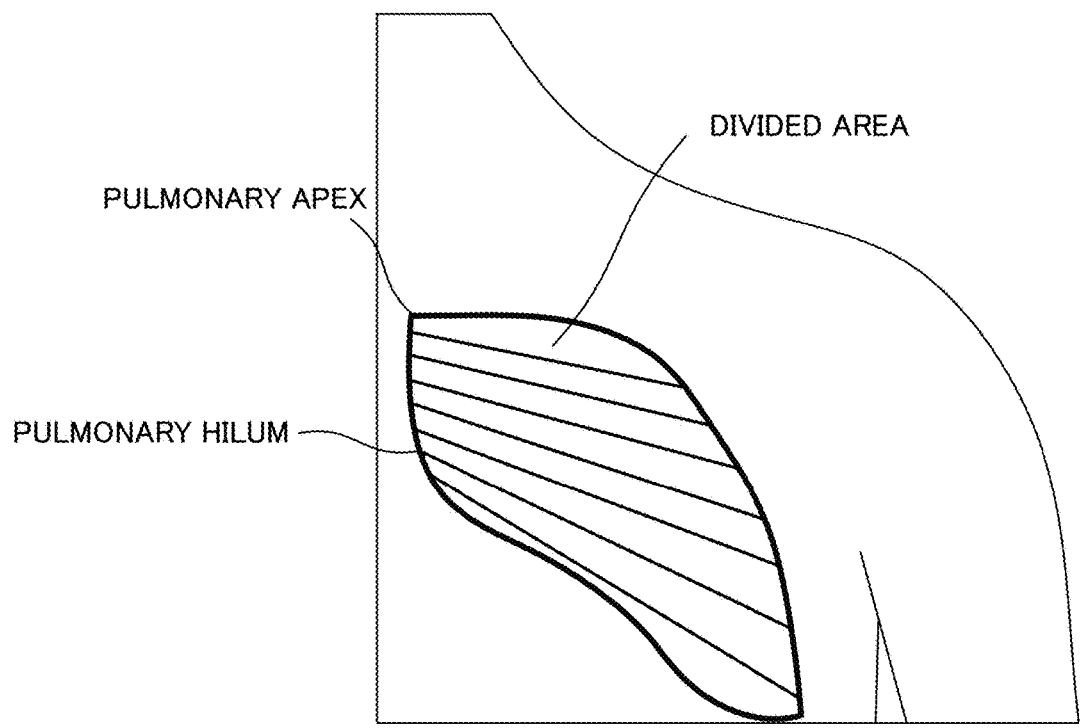
FIG. 1H is a diagram illustrating an example of a division method of a lung area.

A sixth method is a method in which creation of block areas is considered three-dimensionally. As illustrated in FIG. 1G, it may also be possible to cut the lung in a plurality of planes perpendicular to a straight line connecting the pulmonary apex (or hilum pulmonis) and the diaphragm end portion. Further, in the diaphragm, the trunk portion side moves more than the body surface side, and therefore, it can be said that the spring coefficient of the diaphragm differs depending on the position. Consequently, as illustrated in FIG. 1H, it may also be possible to divide the lung by sets of points (planes) at which the amount of displacement accompanying the movement of the diaphragm is equal. Further, as illustrated in FIG. 1B, it may also be possible to additionally draw lines in the vertical direction or in the transverse direction so as to divide the lung into a plurality of rectangular (square) block areas.

Next, the artifact is removed and image data is interpolated. That is, if a bone or the like is included within the analysis range, the bone or the like appears as noise, and therefore, it is desirable to remove the noise by using a noise-cut filter. In an X-ray image, within the lung field area, X-rays easily permeate on the periphery of the position where neither blood vessel nor bone exists, and therefore, the X-ray image becomes black. That is, the pixel value of the X-ray image becomes high. On the other hand, at the position where a blood vessel and a bone exist, it is hard for the X-rays to permeate, and therefore, the X-ray image becomes white. That is, the pixel value of the X-ray image becomes low. This also applies to the other CT and MRI. Here, from the results of the above-described respiratory cycle analysis, it is made possible to interpolate data by using a value in the same phase based on the waveform per respiration and to remove the artifact.

Figure 2A:
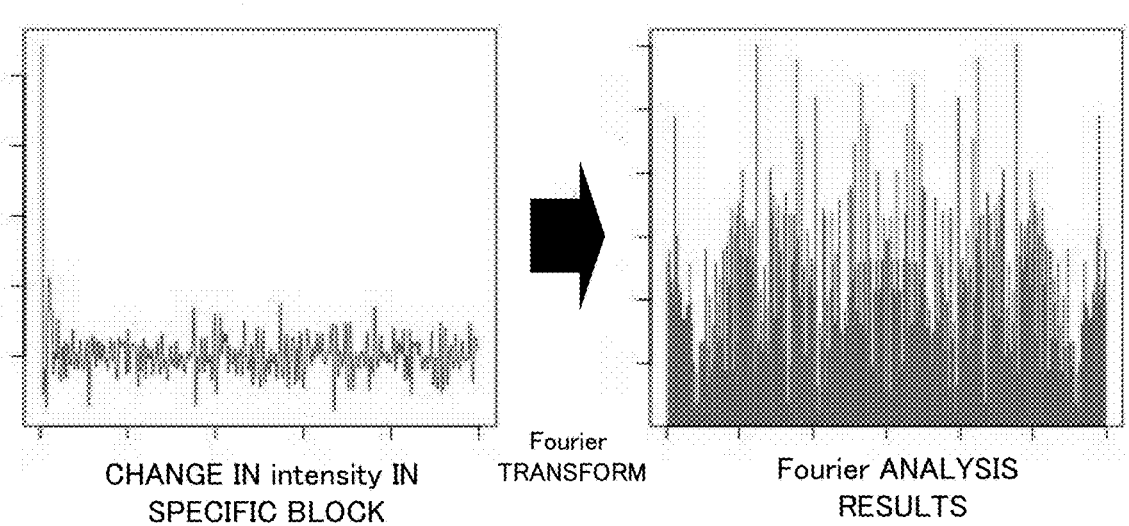
FIG. 2A is a diagram illustrating a change in intensity in a specific block and results of performing a Fourier analysis thereof.
Figure 2B:
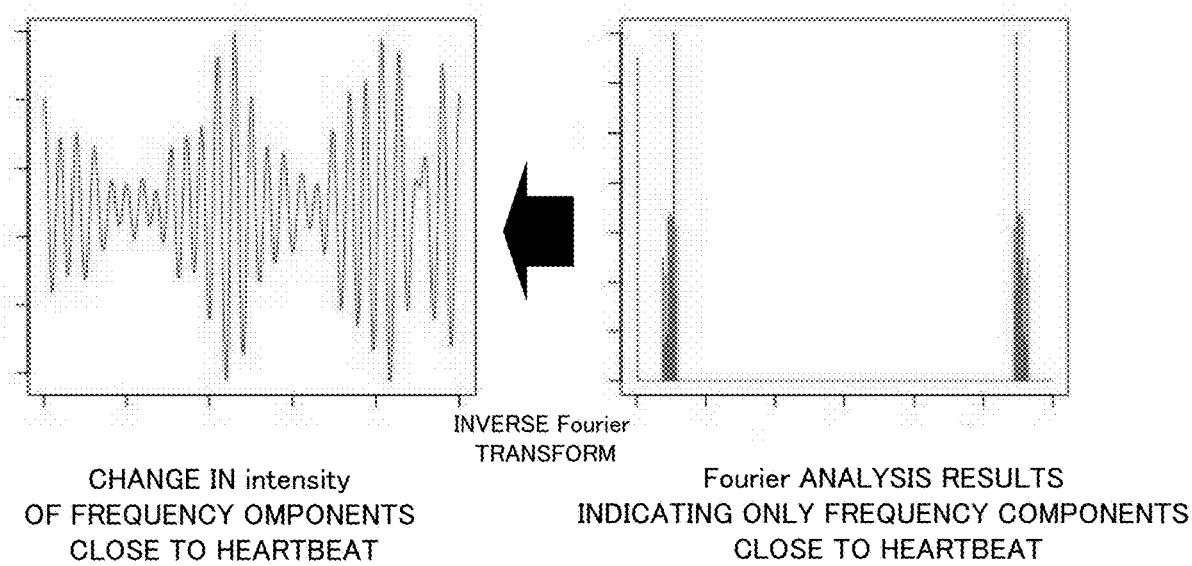
FIG. 2B is a diagram illustrating Fourier transform results of extracting frequency components close to a heartbeat and a change in intensity of the frequency components close to the heartbeat obtained by performing inverse Fourier transform thereof.

Based on the respiratory cycle and the blood vessel beat cycle analyzed as described above, a Fourier analysis is performed for the value of density/intensity in each block area and the amount of change thereof. FIG. 2A is a diagram illustrating a change in intensity in a specific block and results of performing a Fourier analysis thereof. FIG. 2B is a diagram illustrating Fourier transform results of extracting frequency components close to a heartbeat and a change in intensity of frequency components close to the heartbeat obtained by performing inverse Fourier transform thereof. For example, when the change in intensity in a specific block is Fourier-transformed (Fourier analysis), the results as illustrated in FIG. 2A are obtained. Then, by extracting frequency components close to the heartbeat from the frequency components illustrated in FIG. 2A by using, for example, a band-pass filter, the results as illustrated on the right side in FIG. 2B are obtained. By performing inverse Fourier transform for the results, it is possible to obtain the change in intensity in conformity with the change in heartbeat as illustrated on the left side in FIG. 2B.

Note that it is possible to use an AR method (Autoregressive Moving average model) so that calculation is performed in a short time when performing Fourier transform. As the AR method, mention is made of a method of using a Yule-walker equation or a Kalman filter in an autoregressive moving average model and by using Yule-walker estimates derived by the method, a PARCOR method, and a least squares method, it is possible to complement the calculation. Due to this, it is made possible to acquire an image close to a real-time image, to assist the calculation, and to correct the artifact at a higher speed. Due to such a Fourier analysis, it is made possible to extract and display the nature of an image in each block area.

For the blood vessel, the brain wave, and what is recognized as a fixed waveform in other inspections, a waveform analysis is performed. The movement repeated in a fixed state, such as the movement of the foot, is included. For example, in the case of the lung, a difference between left and right is compared. Further, by superimposing Hz of the movement performed repeatedly, whether the same tendency exists is analyzed. By comparing waveform data, the concordance rate of two pieces of data is calculated. Then, the data after a Fourier analysis is compared.

The results of the above-described analysis are visualized and digitized. As the standard uptake, the value is displayed relatively/logarithmically by taking the average value of the measured density/intensity in the entire area of the lung field as 1. Further, because only the direction of the blood flow is employed, the change in a specific direction is cut out. Due to this, it is made possible to take out only data of a significant method. By using the lung field identification results, pseudo colorization is performed following the change in analysis range. That is, in accordance with a specific shape (minimum, maximum, mean, median) fitted to the phase, the analysis results of each individual (subject) are fitted to a relative area. Further, a plurality of analysis results is changed into a specific shape/phase that can be compared. Furthermore, when the standard lung is created, by using the results of the above-described respiratory cycle analysis, the relative position relationship within the lung field is calculated. Note that the standard lung is created by using a line obtained by comprehensively averaging the thorax lines, the density, the diaphragm, and so on, of a plurality of patients. When the standard lung is created, in the case of the lung blood flow, it is possible to measure the distance radially from the hilum pulmonis to the lung end portion. Further, in the case of respiration, it is necessary to perform correction in accordance with the movement of the thorax and the diaphragm. Furthermore, it may also be possible to compositely perform calculation by taking into consideration the distance from the pulmonary apex. Note that, in the present embodiment, the way the entire diaphragm moves is acquired in advance and the necessary movement of the diaphragm is made use of in accordance with the measurement of each region. That is, for the hertz of the movement of the entire diaphragm, respiration synchronization and blood vessel synchronization are taken.

After the standard lung is created, it is made possible to digitize and present the conformity, the concordance rate, and the non-concordance rate. Further, it is possible to display a deviation from the normal state. According to the present embodiment, by performing a Fourier analysis, it is made possible to discover a possibility of a new disease, to compare with oneself in the normal state, to compare one's hand and foot, and to compare one's hand and foot on the opposite side. Further, it is made possible to grasp which portion is abnormal in moving one's foot and in deglutition by digitizing the conformity. Furthermore, it is made possible to determine whether a person in the disease state has changed after a fixed time elapses and in the case where the person has changed, to compare the states before and after the change.

Figure 2C:
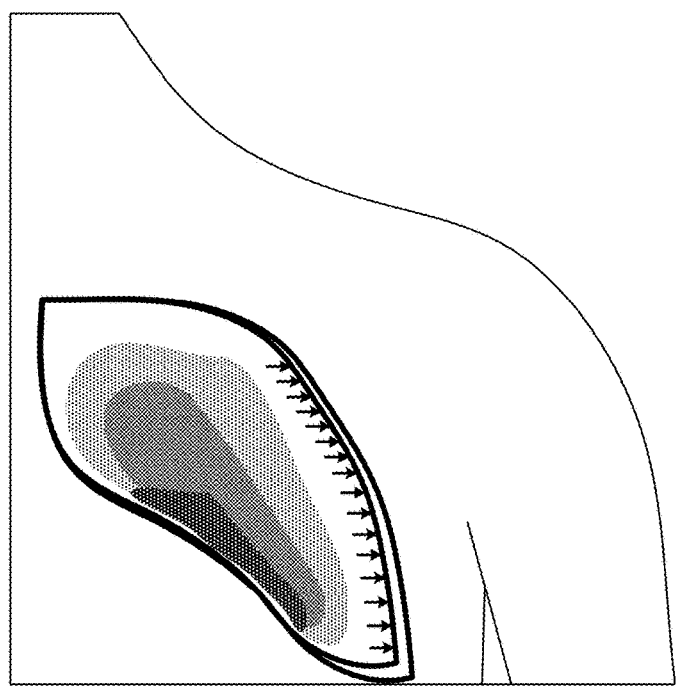
FIG. 2C is a diagram schematically illustrating a change rate of a lung.

As illustrated in FIG. 2C, it is made possible to grasp how many percents the lung differs in the human body when the standard lung is taken to be 100 and to display the change rate. Further, it is also possible to grasp a difference for part of the lung in addition to the entire lung. Furthermore, by performing "Variation classification", it is also possible to specify the standard blood flow. That is, it is made possible to specify the respiratory cycle, to calculate the relative position relationship of the blood vessels, and to specify the blood flow dynamic state of a subject as the standard blood flow.

Due to this, a comparison between a patient and another patient and digitization are enabled. Further, a comparison between the normal lung or normal blood vessel and the typically abnormal pulmonary function or abnormal blood flow and digitization are enabled. Furthermore, as a relative evaluation of the pulmonary function and the lung blood flow at different times of a patient, it is made possible to use the standard lung and the standard blood flow. It is possible to use the standard lung and the standard blood flow such as these as the indexes at the time of evaluation by applying those morphologically to a patient as the standard lung and the standard blood flow by collecting the typical examples of various types of typical patients and healthy persons. Next, the operation of each module according to the present embodiment will be explained.

Figure 3:
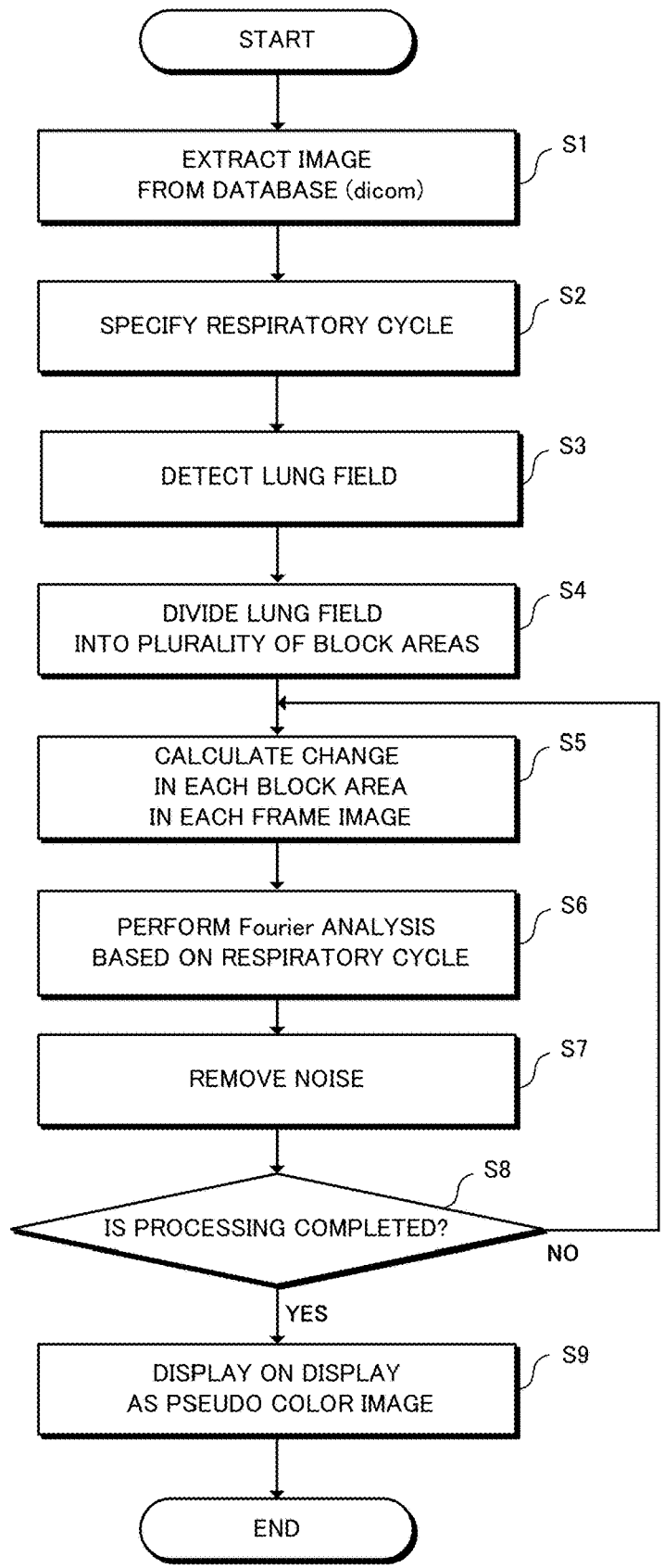
FIG. 3 is a flowchart showing an outline of a respiratory function analysis according to the present embodiment.

First, the respiratory function analysis will be explained. FIG. 3 is a flowchart showing an outline of the respiratory function analysis according to the present embodiment. The basic module 1 extracts images of DICOM from the database 15 (step S1). Here, at least a plurality of frame images included within one respiratory cycle is acquired. Next, in each acquired frame image, by using the density (density/intensity) at least in a fixed area within the lung field, the respiratory cycle is specified (step S2). By fitting a periodic function to this respiratory cycle, the range of the lung field is specified.

It is also possible to specify the respiratory cycle by using the movement of the diaphragm and the movement of the thorax. Further, it may also be possible to use the data obtained from the range consisting of fixed volume density/intensity measured in a region where permeability of X-ray is high and obtained by other measurement methods, such as spirogram.

Next, in FIG. 3, the lung field is automatically detected (step S3). In the automatic detection of the contour of the lung, there is a case where fluctuations occur for each frame image, but by interpolating each frame image based on the respiratory cycle specified at step S2, the lung contour in each frame image is specified. Next, the detected lung field is divided into a plurality of block areas (step S4). Then, a change in each block area in each frame image is calculated (step S5). Here, the value of the change within each block area is averaged and represented as one piece of data. Next, for the value of density/intensity in each block area and the amount of change thereof, a Fourier analysis is performed based on the above-described respiratory cycle (step S6). Due to this, it is made possible to extract and display the nature of the image in each block area.

Next, noise is removed from the results obtained by the Fourier analysis (step S7). The operation at step S5 to step S7 described above is performed once or more times and whether the processing is completed is determined (step S8). In the case where the processing is not completed, a transition is made to step S5 and in the case where the processing is completed, the results obtained by the Fourier analysis are displayed on the display as a pseudo color image (step S9). Further, a white and black image may be displayed. By repeating a plurality of cycles as described above, it is made possible to improve the accuracy of data.

Figure 4:
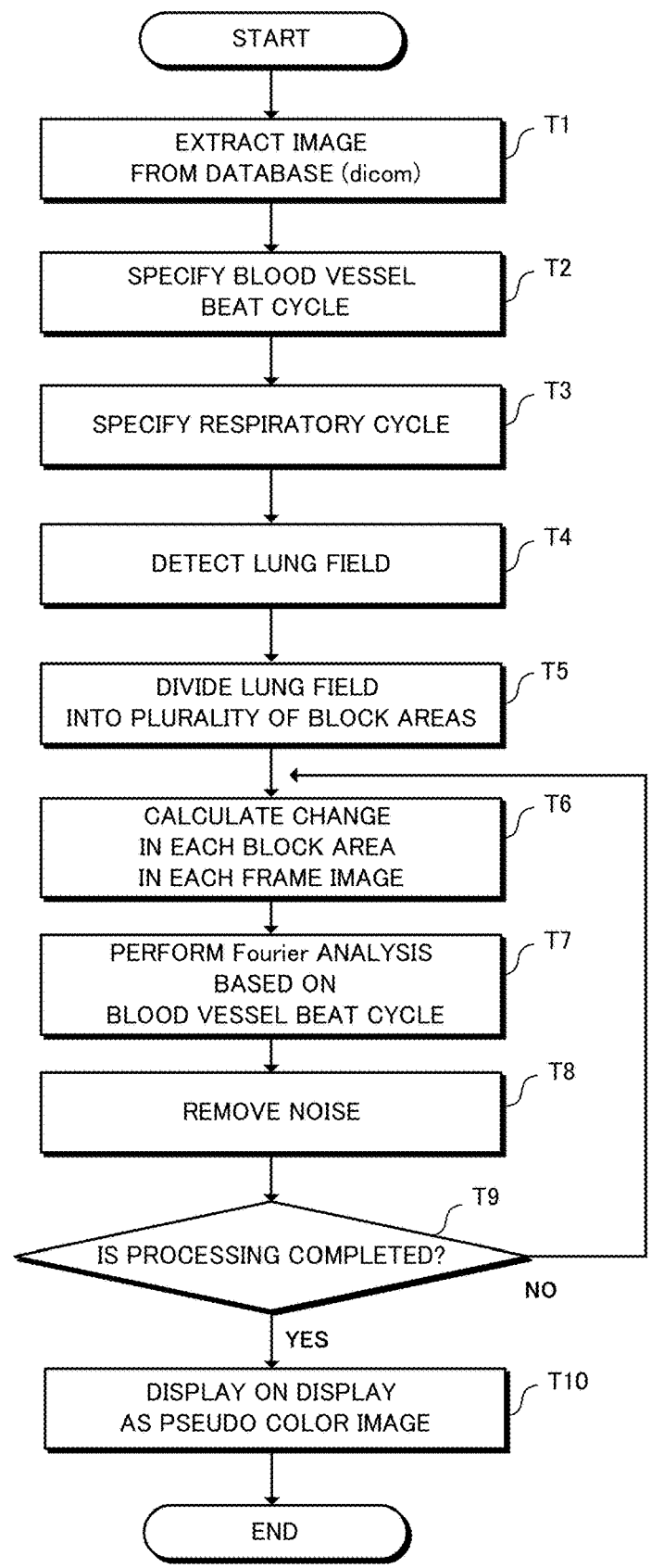
FIG. 4 is a flowchart showing an outline of a lung blood flow analysis according to the present embodiment.

Next, the lung blood flow analysis will be explained. FIG. 4 is a flowchart showing an outline of the lung blood flow analysis according to the present embodiment. The basic module 1 extracts images of DICOM from the database 15 (step T1). Here, at least a plurality of frame images included within one heartbeat cycle is acquired. Next, based on each acquired frame image, the blood vessel beat cycle is specified (step T2). As described above, the blood vessel beat cycle is specified, for example, based on measurement results by other modalities, such as an electrocardiogram and a pulsimeter, or by specifying the heart/hilum pulmonis position/main blood vessel from the lung contour, and the blood vessel beat is analyzed by using a change in density/intensity of each region.

Next, in FIG. 4, the respiratory cycle is specified by the above-described method (step T3) and the lung field is automatically detected by using the respiratory cycle (step T4). In the automatic detection of the lung contour, there is a case where fluctuations occur for each frame image, but by interpolating each frame image based on the respiratory cycle specified at step T3, the lung contour in each frame image is specified. Next, the detected lung field is divided into a plurality of block areas (step T5). Then, a change in each block area in each frame image is calculated (step T6). Here, the value of the change within each block area is averaged and represented as one piece of data. Next, for the value of density/intensity in each block area and the amount of change thereof, a Fourier analysis is performed based on the above-described blood vessel beat cycle (step T7). Due to this, it is made possible to extract and display the nature of the image in each block area.

Next, noise is removed from the results obtained by the Fourier analysis (step T8). The operation at step T6 to step T8 described above is performed once or more times and whether the processing is completed is determined (step T9). In the case where the processing is not completed, a transition is made to step T6 and in the case where the processing is completed, the results obtained by the Fourier analysis are displayed on the display as a pseudo color image (step T10). Further, a white and black image may be displayed. Due to this, it is made possible to improve the accuracy of data.

Figure 5:
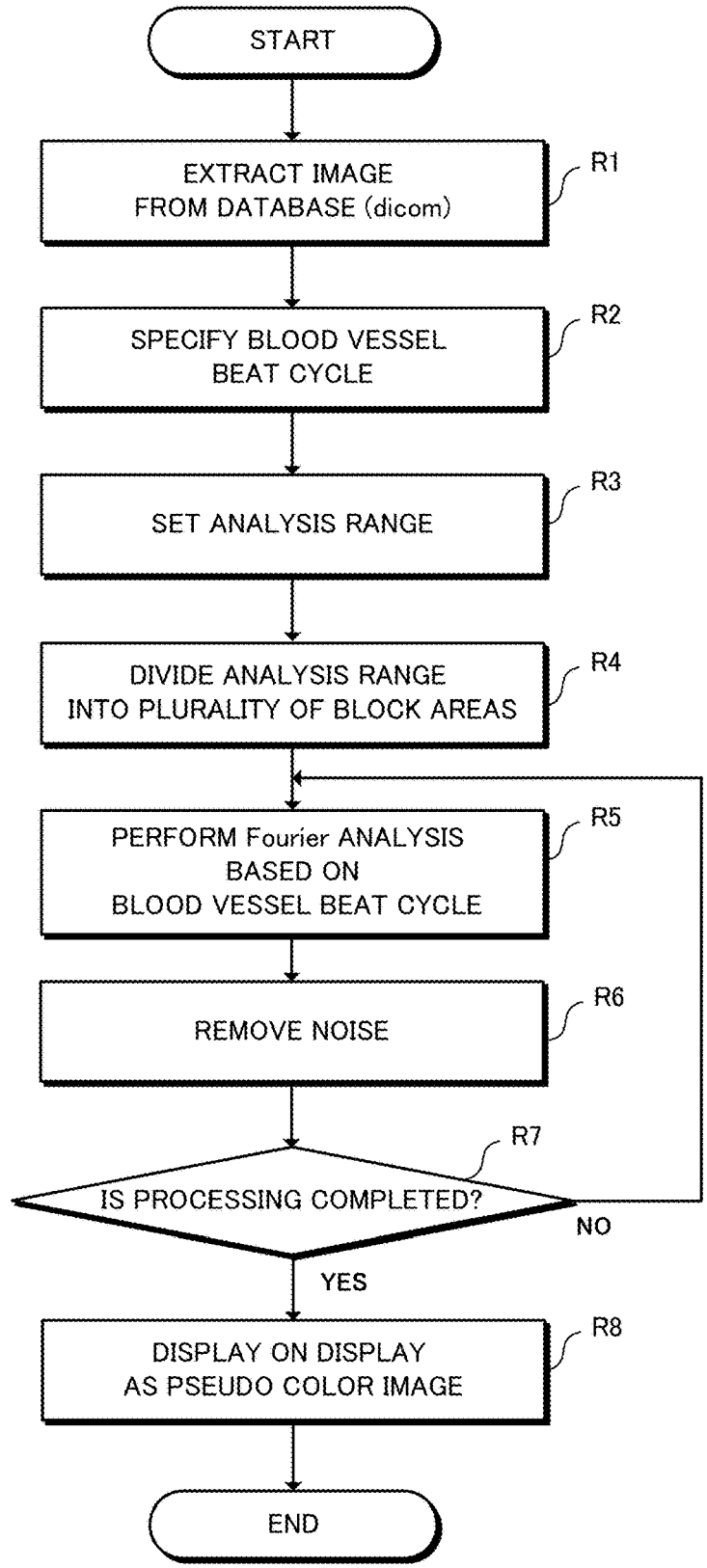
FIG. 5 is a flowchart showing an outline of another blood flow analysis according to the present embodiment.

Next, another blood flow analysis will be explained. It is also possible to apply an aspect of the present invention to the blood flow analysis of the aorta, the abdominal blood vessel, the head internal carotid artery, and so on. FIG. 5 is a flowchart showing an outline of another blood flow analysis according to the present embodiment. The basic module 1 extracts images of DICOM from the database 15 (step R1). Here, at least a plurality of frame images included within one beat cycle is acquired. Next, based on each acquired frame image, the blood vessel beat cycle is specified (step R2). As described above, the blood vessel beat cycle is specified, for example, based on measurement results of other modalities, such as an electrocardiogram and a pulsimeter, or by specifying the heart/hilum pulmonis position/main blood vessel from the lung contour, and the blood vessel beat is analyzed by using a change in density/intensity of each region.

Next, the analysis range is set (step R3) and the set analysis range is divided into a plurality of block areas (step R4). Then, the value of the change within each block area is averaged and represented as one piece of data. Next, for the value of density/intensity in each block area and the amount of change thereof, a Fourier analysis is performed based on the above-described blood vessel beat cycle (step R5). Due to this, it is made possible to extract and display the nature of the image in each block area.

Next, noise is removed from the results obtained by the Fourier analysis (step R6). The operation at step R5 and step R6 described above is performed once or more times and whether the processing is completed is determined (step R7). In the case where the processing is not completed, a transition is made to step R5 and in the case where the processing is completed, the results obtained by the Fourier analysis are displayed on the display as a pseudo color image (step R8). Further, a white and black image may be displayed. Due to this, it is made possible to improve the accuracy of data.

Note that, in the case where consideration is given three-dimensionally as described above, by measuring the respiration rate, the cardiac output, and the center bloodstream by different devices, it is made possible to measure the "partial pulmonary ventilation", the "lung bloodstream", and the "blood flow rate" in each section from those rates. In the case where measurement of the respiration rate, the cardiac output, and the blood flow on the center side is enabled by another modality or the like as quantitative measurement, it is made possible to estimate the estimated function amount by the amount of one frame, its rate, and the amount of change rate in the area. That is, in the case of the respiratory function analysis, estimation of the pulmonary ventilation is enabled by the respiration rate, in the case of the lung blood flow analysis, estimation of the lung bloodstream is enabled by the cardiac output (lung blood vessel output), and in the case of another bloodstream analysis, estimation of the estimated bloodstream (rate) in the branched blood vessel extracted from the bloodstream (rate) on the center side is enabled.

As explained above, according to the present embodiment, it is made possible to evaluate the image of a human body although there are several problems in other modalities, such as CT and MRI, by the photographing method at the present point in time. At least, as to the X-ray moving image device using a flat panel detector, it is possible to perform calculation favorably on the whole by the already existing facility device and the introduction cost is low. Further, in the X-ray moving image device using a flat panel detector, it is made possible to perform inspection of a subject in a simple manner. Furthermore, as to the lung blood flow, screening of the lung thrombus obstruction is enabled. For example, in the X-ray moving image device using a flat panel detector, by executing the diagnosis support program according to the present embodiment before performing CT, it is possible to exclude wasteful inspections. Further, the inspection is simple, and therefore, it is made possible to discover a highly emergent disease in an earlier stage and to deal with it with priority. Furthermore, in other modalities, such as CT and MRI, it is made possible to perform an elaborated diagnosis in each area.

Further, it is also possible to apply the present invention to various blood vessels, for example, to screening of cervical blood flow narrowing and also to blood flow evaluation and screening of great vessels. Further, as to the pulmonary respiration data, the present invention is effective as the partial function inspection of the lung and it is made possible to use the present invention for the pulmonary function inspection. Alternatively, identification of the disease, such as COPD and pulmonary emphysema, is also enabled. Further, it is also made possible to apply the present invention to grasp the properties and condition before and after an operation. Furthermore, by performing a Fourier analysis of the respiratory cycle and the blood flow cycle and removing the waveform of respiration and the waveform of the blood flow in the X-ray image of the abdomen, it is made possible to observe the abnormality of the other biological movements, for example, the intestinal tract ileus.

Note that the present international application is based upon and claims the benefit of priority of the prior Japanese Patent Application No. 2016-141658, filed on Jul. 19, 2016, the entire of which are incorporated herein by reference.

The invention claimed is:

1. A diagnosis support program that analyzes images of a human body and displays analysis results, the program causing a computer to execute:
    processing of acquiring a plurality of frame images from a database that stores the images;
    processing of selecting a specific area from each of the frame images and specifying a respiratory cycle based on pixels in the selected specific area;
    processing of detecting a lung field based on the specified respiratory cycle;
    processing of dividing the detected lung field into a plurality of block areas and calculating a change in image in each of the block areas based on a relative position between each of the block areas and a lung contour;
    processing of Fourier-transforming a change in image in each block area in each of the frame images;
    processing of performing inverse Fourier transform by extracting frequency components corresponding to the respiratory cycle for Fourier transform results of a change in image in each of the block areas; and
    processing of displaying image after the inverse Fourier transform on a display.

2. A diagnosis support program that analyzes images of a human body and displays analysis results, the program causing a computer to execute:
    processing of acquiring a plurality of frame images from a database that stores the images;
    processing of specifying a blood vessel beat cycle of a subject;
    processing of specifying a respiratory cycle based on pixels in a specific area in each of the frame images;
    processing of detecting a lung field based on the specified respiratory cycle;
    processing of dividing the detected lung field into a plurality of block areas and calculating a change in image in a block area in each of the frame images;
    processing of Fourier-transforming a change in image in each block area in each of the frame images;
    processing of performing inverse Fourier transform by extracting frequency components corresponding to the blood vessel beat cycle for Fourier transform results of a change in image in each of the block areas; and
    processing of displaying image after the inverse Fourier transform on a display.

3. A diagnosis support program that analyzes images of a human body and displays analysis results, the program causing a computer to execute:
    processing of acquiring a plurality of frame images from a database that stores the images;
    processing of selecting a specific area from each of the frame images and specifying a blood vessel beat cycle of a subject based on pixels in the selected specific area;
    processing of dividing an analysis range that is set for each of the frame images into a plurality of block areas and calculating a change in image in each block area in each of the frame images;
    processing of Fourier-transforming a change in image in each block area in each of the frame images;
    processing of performing inverse Fourier transform by extracting frequency components corresponding to the blood vessel beat cycle for Fourier transform results of a change in image in each of the block areas; and
    processing of displaying image after the inverse Fourier transform on a display.

4. The diagnosis support program according to claim 1, wherein
    a respiratory cycle of a subject is specified based on a movement of a diaphragm, a movement of a thorax, or data of a spirogram.

5. The diagnosis support program according to claim 2, wherein
    a blood vessel beat cycle of the subject is specified based on measurement results by other modality devices including an electrocardiogram or a pulsimeter, and alternatively, a movement of a diaphragm and a thorax is extracted and a respiratory cycle of a subject is specified based on an image of a diaphragm and an image of a thorax at least included in each of the frame images, a lung field is detected based on the specified respiratory cycle, a position of a heart, a position of a hilum pulmonis, and blood vessel cycles of a main lung blood vessel and a large blood vessel are specified from the detected lung field, and a blood vessel beat cycle is specified based on a change in image of each specified region.

6. The diagnosis support program according to claim 1, wherein
    a relative position relationship between an inside of a lung field and blood vessels is calculated based on the specified respiratory cycle, and a shape of a lung of a subject is specified as a standard lung and a dynamic state of a blood flow of the subject is specified as a standard blood vessel area.

7. The diagnosis support program according to any of claims 1, wherein
    a lung field is divided into a plurality of block areas by plotting a plurality of points in accordance with a fixed rule on opposing contours of a lung field and by connecting opposing points by a segment.

8. The diagnosis support program according to claim 2, wherein
    a respiratory cycle of a subject is specified based on a movement of a diaphragm, a movement of a thorax, or data of a spirogram.

9. The diagnosis support program according to claim 3, wherein
    a blood vessel beat cycle of the subject is specified based on measurement results by other modality devices including an electrocardiogram or a pulsimeter, and alternatively, a movement of a diaphragm and a thorax is extracted and a respiratory cycle of a subject is specified based on an image of a diaphragm and an image of a thorax at least included in each of the frame images, a lung field is detected based on the specified respiratory cycle, a position of a heart, a position of a hilum pulmonis, and blood vessel cycles of a main lung blood vessel and a large blood vessel are specified from the detected lung field, and a blood vessel beat cycle is specified based on a change in image of each specified region.

10. The diagnosis support program according to claim 2, wherein
    a relative position relationship between an inside of a lung field and blood vessels is calculated based on the specified respiratory cycle, and a shape of a lung of a subject is specified as a standard lung and a dynamic state of a blood flow of the subject is specified as a standard blood vessel area.

11. The diagnosis support program according to claim 2, wherein
 a lung field is divided into a plurality of block areas by plotting a plurality of points in accordance with a fixed rule on opposing contours of a lung field and by connecting opposing points by a segment.

12. The diagnosis support program according to claim 3, wherein
 a lung field is divided into a plurality of block areas by plotting a plurality of points in accordance with a fixed rule on opposing contours of a lung field and by connecting opposing points by a segment.

* * * * *